United States Patent [19]

Sagara et al.

[11] 4,284,793

[45] Aug. 18, 1981

[54] METHOD FOR PRODUCING PLASTICIZERS

[75] Inventors: Fumio Sagara; Hiroshi Kawabata; Kiyonori Shiiba, all of Ichiharashi, Japan

[73] Assignee: Chisso Corporation, Osaka, Japan

[21] Appl. No.: 133,863

[22] Filed: Mar. 25, 1980

Related U.S. Application Data

[63] Continuation-in-part of Ser. No. 924,728, Jul. 14, 1978, abandoned.

[30] Foreign Application Priority Data

Nov. 30, 1977 [JP] Japan ................... 52/143368

[51] Int. Cl.³ .................. C07C 67/48; C07C 67/08
[52] U.S. Cl. .................................. 560/78; 560/99
[58] Field of Search ........................... 560/78, 99

[56] References Cited

U.S. PATENT DOCUMENTS

| 2,131,925 | 10/1938 | Ware | 560/78 |
| 2,805,246 | 9/1957 | Bourguignon et al. | 560/78 |
| 3,056,818 | 10/1962 | Werber | 560/410.6 |
| 3,293,282 | 12/1966 | Farrar et al. | 560/191 |
| 3,717,672 | 2/1973 | McGee | 560/191 |
| 3,818,071 | 6/1974 | Chilton | 560/78 |
| 4,007,218 | 2/1977 | Ghanayem | 560/78 |

FOREIGN PATENT DOCUMENTS

| 1469997 | 1/1967 | France | 560/78 |
| 45-35045 | 11/1970 | Japan | 560/191 |
| 46-18027 | 5/1971 | Japan | 560/78 |
| 47-3806 | 2/1972 | Japan | 560/99 |
| 49-135911 | 5/1973 | Japan . | |
| 852110 | 10/1960 | United Kingdom . | |

Primary Examiner—Natalie Trousof
Assistant Examiner—Vera C. Clarke
Attorney, Agent, or Firm—Fred Philpitt

[57] ABSTRACT

A method for producing plasticizers which contain titanium in only a very small amount is provided. According to this method, the amount of waste water is very small. This method comprises reacting phthalic anhydride with an alcohol having 4–18 carbon atoms in the presence of, as a catalyst, a tetraalkyl titanate or a polymer thereof, and has a feature in the treatment of the resultant ester with a solid alkali and adsorbing agent(s) in the absence of water.

5 Claims, No Drawings

METHOD FOR PRODUCING PLASTICIZERS

CROSS REFERENCE TO RELATED APPLICATION

This application is a continuation-in-part application of application Ser. No. 924,728, filed on July 14, 1978 in the United States Patent Office, now abandoned.

BACKGROUND OF THE INVENTION

1. Field of the Invention

This invention relates to a method for producing a plasticizer from the ester obtained by reacting phthalic anhydride with an alcohol having 4-18 carbon atoms in the presence of as a catalyst, a tetraalkyl titanate or a polymer thereof.

2. Description of the Prior Art

The esterification reactions using a tetraalkyl titanate as a catalyst are disclosed in Japanese patent publication No. 3806/1972, Japanese patent application laid-open No. 135911/1974, etc., but the resulting esters obtained according to these reactions are treated in the presence of water, and also such a treatment as blowing-in of steam is carried out for removing the catalyst, and hence the treatment of the esters have had a disadvantage in that the amount of water and the loss of heat energy are both large. Further since the acid value increases in the treatment of blowing-in of steam, there has been also a disadvantage in that addition of an alkali before or after the reactions is required. Further the resultant plasticizer have had a drawback in that the content of titanium therein was high and also the storing-stability was inferior.

U.S. Pat. Nos. 4,007,218 and 3,818,071 both disclose an alkaline treatment of esters prepared in the presence of a titanate catalyst.

With regard to the treatment of esters prepared in the presence of an acidic catalyst, Japanese patent publication No. 18027/1976 discloses a contact treatment of esters with an adsorbent obtained by adding a carrier to an aqueous solution of a carbonate or hydroxide of alkali metals or alkaline earth metals, followed by mixing treatment. Further, U.S. Pat. No. 3,717,672 discloses a treatment of phthalic esters by contacting the phthalic esters with dry slaked lime having associated therewith a very small proportion of an ionizing liquid such as water.

However, in any of these references, it is necessary to employ water or steam at the time of the treatment, and further the characteristic properties of the ester plasticizers such as acid value, color number, volume resisitivity, etc. are insufficient.

Recently, demand for no public nuisance, high quality product and energy saving in chemical industries is strong and plasticizer industry is not exceptional in these points. Accordingly, it is an important problem in producing ester plasticizers, to overcome the above-mentioned drawbacks accompanying the treatment.

It is an object of the present invention to provide a method which is able to overcome the above-mentioned difficult problem in general. It is another object of the present invention to provide a method for producing a plasticizer containing only a small content of titanium, without producing a large amount of waste water.

The method for producing a plasticizer according to the present invention is characterized in treating the ester obtained by reacting phthalic anhydride with an alcohol having 4-18 carbon atoms in the presence of a tetraalkyl titanate or a polymer thereof, with a solid alkali and adsorbing agent(s) in the absence of water.

The alcohols used in the method of the present invention are those having 4-18 carbon atoms and for example, 2-ethylhexanol, n-butanol, isobutanol, heptanol, nonanol, decanol, decyl alcohol and the like can be mentioned.

As tetraalkyl titanate, tetraisopropyl titanate, tetrabutyl titanate, tetraheptyl titanate, tetraoctyl titanate, tetraisodecyl titanate and the like can be mentioned.

The esters of the present invention can be obtained by adding an alcohol to phthalic anhydride and further adding a small amount of a tetraalkyl titanate or its polymer and carrying out the reaction at a high temperature of 150° C. to 250° C. in the atmosphere of an inert gas, taking out formed water to the outside of the system and after reducing the acid value down to 0.1 or less within 3 to 6 hours, and distilling off the alcohol in excess.

The method for producing a plasticizer of the present invention has a feature in the treatment of the above-mentioned ester with a solid alkali and adsorbing agent(s) in the absence of water. As the method for treating esters with a solid alkali and adsorbing agent(s), a method which relies on treating the ester with a solid alkali, followed by treatment with adsorbing agent(s), and a method in which the treatment is carried out with a mixture of a solid alkali and adsorbing agent(s), can be thought of. As the treatment with a solid alkali, there are a method in which an ester is stirred in a treating vessel with a powdered alkali and then an excessive alkali is removed, etc.

The solid alkali used in the method of the present invention, has no particular limitation so long as it is in solid state. Those of powdered form or granular form are preferable, and sodium carbonate, sodium bicarbonate, calcium carbonate, sodium hydroxide, potassium hydroxide, barium carbonate, etc. are useful, but sodium bicarbonate and sodium carbonate are preferable.

The amount of the solid alkali used has also no particular limitation so long as it is an equivalent amount or more to the acid value of the ester. Arbitrary selection is made according to the treating method, but a method in which an ester is contacted with a large excess of a solid alkali in a treating vessel and the excessive alkali is recovered by providing a solid-liquid separator or the like, is preferable. The recovered solid alkali can be used again. The treating temperature is in the range of 100° C.–200° C., preferably 150° C.–200° C., most preferably 170° C.–200° C. and the treating time is 0.5-4 hours.

The treatment of the ester having been treated with a solid alkali, with adsorbing agent(s) is carried out, for example, by adding activated clay with stirring, and then adding diatomaceous earth, followed by filtration. In this case, activated clay and diatomaceous earth are used in the amounts of 0.5-2.0 g and 0.1-1.0 g per Kg of the ester, respectively, aand the treatment is carried out at a temperature of 80° C.–150° C., preferably 80° C.–100° C. for 0.5-2.0 hours. As adsorbing agent(s) used, an activated charcoal can be mentioned in addition to the above-mentioned activated clay and diatomaceous earth. Further, if necessary, it is possible to carry out the alkali treatment and the adsorbing agent treatment simultaneously.

The characteristic feature of the production method of the present invention is that a step of blowing-in of steam, not to mention the water-washing step, is unnecessary and on this account, water, electric power and heat energy can be saved. Further the amount of waste water is exceedingly reduced and the quality of the waste water is improved. Further, the acid value and volume resistivity of resultant plasticizers are superior to those of conventional plasticizers. Further the fact that titanium content is extremely small and preservation stability is good, is also the advantage of this invention.

Following examples are presented to illustrate the present invention which is, however, not intended to limit the scope of the invention.

filtering, to give DOP plasticizer. The results are shown in Table 1.

TABLE 1

|  | Waste water | | DOP plasticizer | | | |
| --- | --- | --- | --- | --- | --- | --- |
|  | Amount ml | *4 BOD ppm | Color APHA | Acid *1 value KOH 1mg/g | Volume *1 resistivity $\Omega \cdot cm \times 10^{-11}$ | Content of titanium CPS *2 |
| Example 1 | 50 | 1500 | 10 | 0.002 | 35 | 190 |
| Comparative Ex. 1 | 180 | 2500 | 20 | 0.02 | 7 | 910 |
| Example 2 | 50 | 1700 | 15 | 0.002 | 30 | 450 |

*1 based upon JIS K-6751
*2 based upon count per second (according to an analytical method of fluorescent X ray)
*4 definition is described after Table 3

EXAMPLE 1

To a 2 l 4-neck flask, 400 g of phthalic anhydride, 914 g of 2-ethylhexanol and 0.43 ml of tetraisopropyl titanate were charged at room temperature, and the temperature of the mixture was elevated to 135° C. with stirring in 30 minutes, during which period monoesterification was carried out. The reaction was further carried out under the stream of nitrogen at temperatures from 135° C. up to 220° C. for 1.5 hours and at a temperature of 220° C. for 3 hours to reduce the acid value to 0.05 KOH mg/g. Then, unreacted 2-ethylhexanol was recovered at 190° C. under a reduce pressure of 20–30 mmHg and 1052.5 g of di-2-ethylhexyl phthalate (hereinafter referred to as DOP) having an acid value of 0.06 was obtained.

To the resultant DOP in an amount of 1052.5 g, 52.6 g of powdered sodium carbonate was added and after stirring at 180° C. for 2 hours, 2.0 g of activated clay was added and stirring was continued at 80° C. for 30 minutes. Then after adding 1.0 g of diatomaceous earth, filtration was carried out to obtain a DOP plasticizer. The amount and BOD of waste water, and the color tone, acid value, volume resistivity and titanium content of the plasticizer are shown in Table 1.

COMPARATIVE EXAMPLE 1

By the process same with that of example 1, 1051 g of DOP having an acid value of 0.07 was obtained. Steam was blown in at 190° C. under a pressure of 20–30 mmHg for 0.5 hour and then 2.0 g of activated clay was added, followed by stirring at 80° C. for 30 minutes, adding of diatomaceous earth in an amount of 1.0 g and

EXAMPLE 2

According to a procedure same with that of example 1, 1052.0 g of DOP having an acid value of 0.04 was obtained. To 1052.0 g of this DOP, 52.6 g of powdered sodium bicarbonate was added. After stirring at 180° C. for 2 hours, 2.0 g of activated clay was added, stirring was continued at 80° for 30 minutes and filtration was carried out after addition of 1.0 g of diatomaceous earth to obtain a DOP plasticizer. The results are also shown in Table 1.

EXAMPLE 3

Phthalic anhydride (800 g), 2-ethylhexanol (1,919 g) and tetraisopropyl titanate (0.90 ml) were fed to a 5 l capacity, 4-neck flask at room temperature and then heated with stirring up to 135° C. over 30 minutes to carry out monoesterification. Thereafter reaction was carried out in nitrogen atmosphere at from 135° C. up to 220° C. over 1.5 hour and further at 220° C. for 3 hours, to give a raw DOP having an acid value (KOH mg/g) of 0.03, followed by recovering unreacted 2-ethylhexanol at 180° C. under a reduced pressure of 10–20 mmHg to obtain 2,106 g of DOP having an acid value of 0.05.

To this DOP (2,106 g) was added 105 g of powdery sodium carbonate, and they were stirred at 175° C. for 2 hours. Thereafter 2.0 g of activated clay was added and stirring was carried out at 80° C. for 40 minutes, followed by adding 1.6 g of diatomaceous earth and then filtration to obtain DOP plasticizer. The amount and BOD of the waste water and the color, acid value, volume resistivity and content of Ti of the DOP plasticizer thus obtained are shown in Table 2.

COMPARATIVE EXAMPLE 2

DOP (2,108 g) of an acid value of 0.05 was prepared in the same manner as in Example 3. To the DOP was added 200 ml of a 10% aqueous solution of sodium hydrogen carbonate, followed by stirring for 2 hours. Thereafter 2.0 g of activated clay was added and stirring was carried out at 80° C. for 30 minutes, followed by adding 1.6 g of diatomaceous earth and filtration to obtain DOP plasticizer. The results are also shown in Table 2.

TABLE 2

|   | Waste water | | DOP plasticizer | | | |
|---|---|---|---|---|---|---|
|   | Amount ml | *4 BOD ppm | Color APHA | Acid *1 value KOH 1mg/g | Volume *1 resistivity $\Omega \cdot cm \times 10^{-11}$ | content of titanium CPS *2 |
| Example 3 | 98 | 1600 | 10 | 0.003 | 30 | 200 |
| Comparative Ex. 2 | 296 | 3000 | 20 | 0.002 | 10 | 300 |

*1 and *2 have the same meanings as those in Table 1.

EXAMPLE 4

A monester reaction liquid (5,900 Kg/hr) prepared by feeding molten phthalic anhydride (1,900 Kg/hr) and 2-ethylhexanol (4,000 Kg/hr), and tetraisopropyl titanate (2.5 Kg/hr) were continuously fed to a reaction apparatus of continuous stirring vessel type to obtain a raw diesterification reaction liquid having an aacid value of 0.04.

Excess 2-ethylhexanol in the raw reaction liquid was distilled off by means of an evaporator and recovered to obtain a raw DOP.

This raw DOP (5,000 Kg/hr) and powdery sodium carbonate (60 Kg/hr) were continuously fed to a treating vessel where treatment was carried out at 180° C. for one hour, followed by cooling down to about 80° C.

Thereafter activated clay (5 Kg/hr) and diatomaceous earth (5 Kg/hr) were continuously fed and mixed with stirring to obtain a slurry, which was then filtered by a filter precoated in advance with diatomaceous earth to obtain 5,000 Kg/hr of DOP plasticizer.

The qualities of DOP thus obtained and data relative to waste water are shown in Table 3.

COMPARATIVE EXAMPLE 3

Raw DOP obtained in the same manner as in Example 4 was cooled down to about 80° C., without treating with powdery sodium carbonate, followed by filtration in the same manner as in Example 4 to obtain DOP plasticizer. The results are shown in Table 3.

COMPARATIVE EXAMPLE 4

Steam (15 Kg/hr) was blown into raw DOP (5,000 Kg/hr) obtained in the same manner as in Example 4 and having an acid value of 0.04, at 180° C. under a reduced pressure of 5 mmHg to continuously carry out stirring treatment. After the treatment for 30 minutes, the resulting treated liquid was cooled down to about 80° C., followed by the same treatments as in Example 4 to obtain 5,000 Kg/hr of DOP plasticizer. The results are shown in Table 3.

COMPARATIVE EXAMPLE 5

Raw diesterification reaction liquid (5,700 Kg/hr) obtained in the same manner as in Example 4 was neutralized with a 20% aqueous solution of sodium hydroxide (10 Kg/hr) and washed with deionized water (about 2 m³/hr), followed by separating oil layer from aqueous layer. Water and excess 2-ethylhexanol were distilled off by means of an evaporator to obtain raw DOP.

This DOP was filtered in the same manner as in Example 4 to obtain DOP plasticizer. The results are shown in Table 3.

TABLE 3

|   | Waste water | | DOP plasticizer | | | |
|---|---|---|---|---|---|---|
|   | Amount ml | *4 BOD ppm | Color APHA | Acid *1 value KOH 1mg/g | Volume *1 resistivity $\Omega \cdot cm \times 10^{-11}$ | content of titanium CPS *3 |
| Example 4 | 740 | 1620 | 15 | 0.007 | 15 | 0.1 |
| Comparative Ex. 3 | 740 | 1620 | 15 | 0.02 | 0.2 | 13 |
| Comparative Ex. 4 | 755 | 1690 | 15 | 0.09 | 1.4 | 0.1 |
| Comparative Ex. 5 | 2240 | 5630 | 15 | 0.008 | 8 | 0.1 |

*1 has the same meaning as in Table 1.
*3 According to diantipyrylmethane colorimetry
*4 BOD (Biochemical Oxygen Demand) value is measured according to JIS K 0102 wherein a sample is diluted with oxygen-saturated water; the resulting material is allowed to stand in a constant temperature bath at 20° C. for 5 days; and the amount of dissolving oxygen reduced is measured according to a modification of Winkler's method employing sodium azide to calculate the amount of oxygen consumed (ppm).

What is claimed is:

1. In a method for producing dialkyl phthalate plasticizer by esterification in the presence of a tetraalkyl titanate, followed by treatment of the resulting ester with adsorbent(s) and filtration,
the improvement which comprises:
   (1) reacting phthalic anhydride with an alkanol having 4–18 carbon atoms at a temperature of 150° C.–250° C., for 3–6 hours, in the presence of a tetraalkyl titanate or its polymer to obtain a dialkyl phthalate having an acid value of 0.1 or lower and distilling off the remaining unreacted alkanol from the resulting phthalate at a high temperature and under a reduced pressure;
   (2) subjecting the dialkyl phthalate obtained from the step (1), without the conventional treatment of blowing steam into said dialkyl phthalate after said distilling off, to a contact treatment with a solid alkali selected from the group consisting of sodium carbonate, sodium bicarbonate, calcium carbonate, barium carbonate, sodium hydroxide and potassium hydroxide, in the absence of water, at a temperature of 100° C. to 200° C.;

(3) treating the resulting liquid obtained in said contact treatment, with adsorbent(s); and (4) separating the dialkyl phthalate from the resulting material by filtration.

2. A method according to claim 1 wherein the amount of said solid alkali employed is an equivalent amount or more to the acid value of the phthalate obtained in the step (1).

3. A method according to claim 1 wherein said solid alkali is powdery aand said contact treatment of the step (2) is carried out by mixing this powdery solid alkali with the phthalate obtained in the step (1) with stirring to remove excess alkali.

4. A method according to claim 1, claim 2 or claim 3 wherein said adsorbent(s) are activated clay and diatomaceous earth and the treatment of the step (3) is carried out at a temperature of 80° to 150° C.

5. A method according to claim 4 wherein said activated clay and diatomaceous earth are employed in amounts of 0.5 to 2.0 g and 0.1 to 1.0 g based on 1 kg of the dialkyl phthalate, respectively.

* * * * *